United States Patent [19]

Kummer et al.

[11] 4,305,888

[45] Dec. 15, 1981

[54] MANUFACTURE OF SALTS OF DICARBOXYLIC ACIDS AND DIAMINES

[75] Inventors: Rudolf Kummer, Frankenthal; Rolf Platz, Mannheim; Heinz-Walter Schneider, Ludwigshafen, all of Fed. Rep. of Germany

[73] Assignee: BASF Aktiengesellschaft, Fed. Rep. of Germany

[21] Appl. No.: 813,971

[22] Filed: Jul. 8, 1977

[30] Foreign Application Priority Data

Aug. 28, 1976 [DE] Fed. Rep. of Germany ....... 2638824

[51] Int. Cl.³ .............................................. C07C 87/14
[52] U.S. Cl. .................................................. 260/501.2
[58] Field of Search .................... 260/404.5 PA, 501.2

[56] References Cited

U.S. PATENT DOCUMENTS

| | | | |
|---|---|---|---|
| 2,130,947 | 9/1938 | Carothers | 260/501.2 |
| 2,425,392 | 8/1947 | Robinson et al. | 260/404.5 |
| 3,884,947 | 5/1975 | Badin et al. | 260/404.5 |
| 3,952,051 | 4/1976 | Ogawa et al. | 260/501.2 |

OTHER PUBLICATIONS

Morrison and Boyd Organic Chemistry 3rd Ed. pp. 680–681, 1973.
Journal of the American Chemical Society, vol. 60, p. 51 (1938).
Houben Weyl, Methoden der Organischen Chemie, vol. 8, pp. 658–659 (1953).
Comptes Rendus, vol. 100, p. 946 (1885).

*Primary Examiner*—John F. Niebling
*Attorney, Agent, or Firm*—Keil & Witherspoon

[57] ABSTRACT

A process for the manufacture of salts of alkanedicarboxylic acids of 4 to 12 carbon atoms and alkanediamines of 3 to 14 carbon atoms, comprising reacting esters of alkanols of 1 to 4 carbon atoms and alkanedicarboxylic acids of 4 to 12 carbon atoms with alkanediamines of 3 to 14 carbon atoms in stoichiometric amounts in the presence of water at an elevated temperature, with continuous removal of the alkanols formed, in which process the reaction is carried out, from the start, in the presence of the particular salt of alkanedicarboxylic acid and alkanediamine which is to be manufactured.

7 Claims, No Drawings

MANUFACTURE OF SALTS OF DICARBOXYLIC ACIDS AND DIAMINES

The present invention relates to a process for the manufacture of salts of alkanedicarboxylic acids of 4 to 12 carbon atoms and alkanediamines of 3 to 14 carbon atoms, by reacting alkanedicarboxylic acid esters with alkanediamines.

Salts of dicarboxylic acids and diamines, eg. hexamethylenediammonium adipate, are used extensively for the manufacture of nylons. The conventional method of manufacturing, for example, hexamethylenediammonium adipate is to react adipic acid with hexamethylenediamine in aqueous solution. Since the manufacture of adipic acid via the oxidation of cyclohexane to give cyclohexanol results is considerable amounts of non-utilizable waste products, which must be disposed of, attempts have been made to fine other methods of manufacturing dicarboxylic acids. Adipic acid diesters can be manufactured in a simple manner, which virtually avoids the production of non-utilizable waste products, via the carbonylation of butadiene in the presence of alkanols. Electrochemical methods can also be used to obtain alkanedicarboxylic acid esters without forming waste products.

It is an object of the present invention to manufacture salts of dicarboxylic acids with alkanediamines from alkanedicarboxylic acid esters without first converting these esters to the free acid.

It is true that German Published Application DAS No. 1,203,466 discloses the reaction of dicarboxylic acid esters with diamines in the stoichiometric ratio in the presence of water of from 120° to 160°. However, this does not result in the salts of alkanedicarboxylic acids and alkanediamines, but in prepolymers.

We have found that the above object is achieved, and that salts of alkanedicarboxylic acids of 4 to 12 carbon atoms and alkanediamines of 3 to 14 carbon atoms are obtained in an advantageous manner by reacting alkyl esters (where alkyl is of 1 to 4 carbon atoms) of alkanedicarboxylic acids of 4 to 12 carbon atoms with alkanediamines of 3 to 14 carbon atoms at elevated temperatures in the presence of water, with continuous removal of the alkanols formed, if the reaction is carried out, from the start, in the presence of the particular salt of alkanedicarboxylic acid and alkanediamine which is to be manufactured.

The new process has the advantage that the alkanedicarboxylic acid esters are directly converted to the corresponding salts with alkanediamines without first having to manufacture free alkanedicarboxylic acids.

The process of the invention is surprising inasmuch as it was to be expected from German Published Application DAS No. 1,203,466 that a hydrolytic scission of the esters would only take place at acceptable speeds at high temperatures, above 120°, and that in any case not the corresponding salts, but prepolymers, would be obtained.

The starting materials used are esters of alkanols of 1 to 4 carbon atoms with alkanedicarboxylic acids of 4 to 12 carbon atoms. Those derived from $\alpha,\omega$-alkanedicarboxylic acids, especially those having an unbranched carbon chain, are preferred. Esters of alkanols of 1 to 4 carbon atoms with alkanedicarboxylic acids of 6 to 12 carbon atoms are particularly preferred. Methyl esters and ethyl esters, preferably methyl esters, of alkanedicarboxylic acids of the above number of carbon atoms have proved to be particularly suitable. Examples of suitable dicarboxylic acid esters are dimethyl glutarate, dimethyl adipate, diethyl suberate, dibutyl sebacate and dimethyl dodecanedicarboxylate. Dimethyl adipate and dimethyl sebacate have attained particular industrial importance.

The diamines used are alkanediamines of 3 to 14 carbon atoms. Preferred diamines are $\alpha,\omega$-alkanediamines, especially those having a straight carbon chain. The use of alkanediamines of 4 to 12 carbon atoms is particularly preferred. Examples of suitable amines are hexamethylenediamine, tetramethylenediamine, heptamethylenediamine, octamethylenediamine, decamethylenediamine and dodecanemethylenediamine. Hexamethylenediamine has attained particular industrial importance.

When the salts produced are to be used for the manufacture of nylons, the dicarboxylic acid esters and diamines are employed in stoichiometric amounts.

The reaction is carried out in the presence of water. Advantageously, at least 10 moles of water are employed per mole of dicarboxylic acid ester. As a rule, the amount of water is from 10 to 50 moles per mole of dicarboxylic acid ester. The amount of water also depends on the concentration of the salt solution to be produced since, for example, hexamethylenediammonium adipate is further processed as an aqueous solution of from 50 to 60% strength by weight, without isolating the salt.

An essential feature of the invention is that the reaction is carried out, from the start, in the presence of the particular salt of alkanedicarboxylic acid and alkanediamine which is to be manufactured. Advantageously, the total amount of water used contains from 5 to 30, especially from 10 to 20,% by weight of the particular salt. The pH is preferably kept below 10, for example at from 7 to 9.5, during the reaction in the aqueous solution. The pH can be adjusted by varying the amount of the salt of alkanedicarboxylic acid and alkanediamine used, as a result of the buffer action of the salt. Obviously, the pH should, after completion of the reaction, correspond to the equivalence point of the particular salt, eg. from 7.7 to 7.8 in the case of hexamethylenediammonium adipate or from 7.6 to 7.7 in the case of hexamethylenediammonium sebacate.

The reaction is preferably carried out at from 40° to 120° C., 60° to 100° C. being particularly advantageous. The alkanols formed in the reaction are continuously removed from the reaction mixture, eg. by distilling them off. As a rule, the reaction is carried out under atmospheric pressure but it is also possible to work under reduced or superatomspheric pressure. The alkanols distilled from the reaction mixture, eg. methanol, can be re-used for the carbonylation of butadiene.

As a rule, the reaction takes from 2 to 5 hours.

The aqueous solutions of salts of dicarboxylic acid with diamines, which are obtained by the process of the invention and which contain for example from 40 to 60% by weight of salt, can be used without isolating the salt. However, it is also possible to isolate the salts of dicarboxylic acids with diamines from the reaction mixture obtained, eg. by evaporation and cooling.

Salts of dicarboxylic acids with diamines which are manufactured according to the invention may be used for the manufacture of nylons.

The Examples which follow illustrate the process of the invention. In the Examples, parts are by weight and bear the same relation to parts by volume as the kilogram to the liter.

EXAMPLE 1

69.6 parts of dimethyl adipate are added to a solution containing 157 parts of the salt of hexamethylenediamine and adipic acid (AH salt) in 275 parts of water, and the mixture is then heated to about 95° C. 46.4 parts of hexamethylenediamine in 310 parts of water are run in over 10 minutes. The temperature is gradually raised to 100° C. and the methanol is continuously distilled from the reaction mixture at the rate at which it is formed. In the course of 4 hours, a total of 32 parts of methanol are obtained, and at the same time the pH of the solution drops to 7.8. Potentiometric titration, shows that all the nitrogen present in solution is in the form of an alkylammonium ion, ie. that prepolymers having an acid amide structure have not been formed.

On concentrating and cooling the aqueous solution, hexamethylenediammonium adipate, having a melting point of 195° C., is obtained.

After diluting the solution with water, it can be re-used for the manufacture of further salt.

EXAMPLE 2

Using a procedure similar to that employed in Example 1, 92 parts of dimethyl sebacate are added to a solution which contains 191 parts of the salt of hexamethylenediamine and sebacic acid in 467 parts of water. 46.4 parts of hexamethylenediamine in 310 parts of water are run in over 1 hour whilst stirring and heating to 100° C. The solution is then stirred for about 5 hours at 100° C. whilst distilling off the methanol; in the course thereof, the pH drops to 7.7 Titration again shows that the entire nitrogen is present in the form of the ammonium salt. Free amine and prepolymer are not present. The solution is clear and colorless at room temperature.

EXAMPLE 3

The salt of adipic acid and 1,3-diaminopropane is prepared as described in the preceding Examples.

132 parts of salt are introduced into 397 parts of water and 69.6 parts of dimethyl adipate are then added. 29.7 parts of diaminopropane in 198 parts of water are run in over 1 hour at 100° C., and the mixture is stirred for a further 4 hours whilst distilling off the methanol. In the course thereof, the pH of the solution drops to 7.0, which shows that neither free diamine nor prepolymers are present. The solution is clear and colorless.

We claim:

1. A process for the manufacture of salts of alkanedicarboxylic acids of 4 to 12 carbon atoms and alkanediamines of 3 to 14 carbon atoms, comprising reacting esters of alkanols of 1 to 4 carbon atoms and alkanedicarboxylic acids of 4 to 12 carbon atoms with alkanediamines of 3 to 14 carbon atoms in the presence of at least 10 moles of water per mole of alkanedicarboxylic acid ester at from 40° to 120° C. with continuous removal of the alkanols formed, in which process the reaction is carried out, from the start, in the presence of the particular salt of alkanedicarboxylic acid and alkanediamine which is to be manufactured.

2. The process of claim 1, in which dimethyl adipate or dimethyl sebacate and hexamethylenediamine are used as starting materials.

3. The process of claim 1, in which from 10 to 50 moles of water are used per mole of alkanedicarboxylic acid ester.

4. The process of claim 1, in which a temperature of from 60° to 100° C. is maintained.

5. The process of claim 1, in which the total amount of water used contains from 5 to 30% by weight of the particular salt of alkanedicarboxylic acid and alkanediamine to be manufactured.

6. The process of claim 1, in which a pH of from 7 to 9.5 is maintained.

7. The process of claim 1, in which the ester and amine are used in stoichiometric amounts.

* * * * *